United States Patent [19]

Gowan, Jr.

[11] Patent Number: 5,374,659

[45] Date of Patent: Dec. 20, 1994

[54] AQUEOUS PHARMACEUTICAL SUSPENSION FOR SUBSTANTIALLY WATER INSOLUBLE PHARMACEUTICAL ACTIVES

[75] Inventor: Walter G. Gowan, Jr., Glenside, Pa.

[73] Assignee: McNeil-PPC, Inc., Milltown, N.J.

[21] Appl. No.: 219,009

[22] Filed: Mar. 28, 1994

Related U.S. Application Data

[63] Continuation of Ser. No. 675,122, Mar. 25, 1991, abandoned, which is a continuation of Ser. No. 372,734, Jun. 28, 1989, abandoned.

[51] Int. Cl.$^5$ ............... A61K 31/19; A61K 47/44
[52] U.S. Cl. ........................ 514/557; 514/404;
    514/410; 514/420; 514/423; 514/778; 424/466;
    424/467; 424/469; 424/439
[58] Field of Search ............ 514/404, 410, 420, 423,
    514/557, 778; 424/466, 467, 409, 439

[56] References Cited

U.S. PATENT DOCUMENTS

| | | | |
|---|---|---|---|
| 3,228,831 | 1/1966 | Nicholson et al. | 167/53 |
| 3,385,886 | 5/1968 | Nicholson et al. | 260/515 |
| 3,911,128 | 10/1975 | Buzzolini | 514/261 |
| 4,145,440 | 5/1979 | Fitch et al. | 424/287 |
| 4,259,316 | 5/1981 | Nakashima | 424/52 |
| 4,335,102 | 6/1982 | Nakashima | 424/52 |
| 4,346,108 | 8/1982 | Singer | 424/317 |
| 4,361,580 | 11/1982 | Peck et al. | 424/287 |
| 4,447,454 | 5/1984 | Lednicer | 564/306 |
| 4,542,158 | 9/1985 | Dorn | 514/512 |
| 4,684,666 | 8/1987 | Haas | 514/557 |
| 4,744,986 | 5/1988 | Luber et al. | 424/156 |
| 4,761,274 | 2/1988 | Denick, Jr. et al. | 424/48 |
| 4,762,709 | 8/1988 | Sheumaker | 424/79 |
| 4,788,220 | 11/1988 | Mody et al. | 514/557 |
| 4,882,169 | 11/1989 | Ventouras | 424/451 |
| 4,886,669 | 12/1989 | Ventouras | 424/469 |

FOREIGN PATENT DOCUMENTS

| | | |
|---|---|---|
| 52269/90 | 4/1990 | Australia . |
| 2189142 | 10/1987 | United Kingdom . |
| WO8606626 | 11/1986 | WIPO . |
| WO89/03210 | 4/1989 | WIPO . |

OTHER PUBLICATIONS

Merk Index pp. 127, 280–281 (1976).
Remington's Pharmaceutical Sciences, Chapter 17, pp. 229–230 (1975).

*Primary Examiner*—Celia Chang

[57] ABSTRACT

The present invention relates to an aqueous pharmaceutical suspension composition comprising: from about 0.2% to 20% of a substantially water insoluble pharmaceutical active, e.g. ibuprofen; a suspension stabilizing effective amount of xanthan gum, pregelatinized starch and polyoxyethylene sorbitan monooleate; an effective amount of taste masking composition; and water, as well as a process for producing such aqueous pharmaceutical suspensions.

13 Claims, No Drawings

AQUEOUS PHARMACEUTICAL SUSPENSION FOR SUBSTANTIALLY WATER INSOLUBLE PHARMACEUTICAL ACTIVES

This is a continuation-in-part, division, of application Ser. No. 07/675,122, filed Mar. 25, 1991, now abandoned which is a continuation of application Ser. No. 07/372,734, Jun. 28, 1989 now abandoned.

FIELD OF THE INVENTION

This invention relates to aqueous pharmaceutical suspension compositions. More particularly, the invention relates to a taste masked pharmaceutical suspension comprising substantially water insoluble pharmaceutical actives, suspension agents and taste masking agents and a process for making such taste masked liquid pharmaceutical suspensions.

BACKGROUND OF THE INVENTION

Orally administered medicaments are given to the patient in many forms, including solid form such as capsules, caplets or tablets and liquid form such as solutions, emulsions or suspensions. Medicaments administered in solid form are usually intended to be swallowed whole, therefore, the often disagreeable taste of the active ingredient need not be taken into account in formulating the medicine, except for the provision of means to prevent the taste from being apparent during the short time the medicine is in the mouth. Such means may include the provision of an appropriately thin and quickly dissolving coating on a tablet or caplet or the use of a gelatin capsule form, (the gelatin outer shell of the capsule keeps the active ingredient inside until the capsule has been swallowed), or simply compressing a tablet firmly so that it will not begin to disintegrate during the short time that it is intended to be in the mouth. Children, older persons, and many other persons including disabled or incapacitated patients have trouble swallowing whole tablets and even capsules. Therefore, in cases where the dosage to be administered cannot be made into a very small tablet or capsule, it is desirable to provide the medicine either in a chewable solid form or a liquid form. For many patients, including pediatric and geriatric patients, a liquid oral dosage form is preferable over chewable dosage form because of the ready swallowability without chewing of the liquid dosage form.

A common problem associated with liquid dosage forms is the often disagreeable taste of the active ingredients which manifest itself during the time that the liquid dosage form is in the mouth prior to swallowing. In some cases, the taste of the active medicament in a liquid form is generally overpowered by adding flavoring ingredients to the liquid so that when it is swallowed the bitter or unpleasant taste of the medicament is masked. For instance, this has been done with a pediatric liquid dosage form of acetaminophen (N-acetyl para-aminophenol or "APAP"). APAP is available commercially in an aqueous solution that includes overpowering flavor ingredients that masked the unpleasant taste of the APAP.

Aqueous solutions are generally stable and easy to prepare for water soluble actives, such as APAP, but it is difficult to prepare water insoluble pharmaceutical actives in storage stable ready-to-use liquid dosage form. Water insoluble ingredients present in water based solutions tend to separate or settle out and even shaking before administration does not insure a consistently accurate dosage regimen. While some water insoluble medicaments are soluble in alcohol, and may be presented in alcohol solutions, it is more desirable, particularly in pediatric dosage forms, to use aqueous "alcohol free" solutions.

The present invention is directed to discovery of a stable aqueous suspension system for water insoluble pharmaceutical actives which when combined with taste masking compositions achieve a palatable dosage form for both geriatric and especially pediatric applications.

SUMMARY OF THE INVENTION

As embodied and fully described herein the present invention provides an aqueous pharmaceutical suspension composition consisting essentially of from about 0.2% to 20.0% by weight by volume of a substantially water insoluble pharmaceutical active; a suspension stabilizing effective amount of xanthan gum; pregelatinized starch and polyoxyethylene sorbitan monooleate; an effective amount of a taste masking composition selected from the group consisting of sugars, sweet polyhydric alcohols, glycerin, artificial sweetener, flavoring agents and mixtures thereof; and water.

In preferred embodiments the invention comprises about 0.13 to 0.24% xanthan gum, 1.05 to 1.60% pregelatinized starch and 0.01 to 1.00% polyoxyethylene sorbitan monooleate by weight by volume of the total suspension and the substantially water insoluble pharmaceutical active is preferably ibuprofen and comprises about 0.4% to 10% by weight by volume. In further preferred embodiments of the invention the taste masking composition comprises from about 20 to 35% sucrose, from about 0 to 10% sorbitol and from about 5 to 30% glycerin weight by volume of the total suspension. Preferably citric acid, or a pharmaceutically acceptable salt thereof is added to the suspension in an amount to stabilize the pH of the solution at between 3.5 and 5.0.

As embodied and fully described herein the present invention also provides a process for preparing an aqueous pharmaceutical suspension composition comprising the sequential steps consisting essentially of:

(a) dry blending from about 0.13 to 0.24% xanthan gum, about 1.05 to 1.60% pregelatinized starch and from about 4% to 7% sugar, preferably sucrose, by weight by volume of the total suspension;

(b) separately mixing about 50% water, 5 to 30% glycerin, and 0 to 10% of a sweet polyhydric alcohol, preferably sorbitol, by weight by volume of the total suspension;

(c) adding the dry blend of step (a) with the aqueous mixture of step (b) and mixing until the xanthan gum and pregelatinized starch are uniformly dispersed throughout the mixture;

(d) adding from about 16 to 28% sugar, preferably sucrose, by weight by volume of the total suspension to the dispersion of step (c) and mixing until the ingredients are uniformly dispersed in the mixture;

(e) admixing about 0.01 to 1.00% polyoxyethylene sorbitan monooleate, and 0.2 to about 20.0% of a substantially water insoluble pharmaceutical active by weight by volume of the total suspension and sufficient citric acid to stabilize the pH of the solution at between about 3.5 to 5.0, with the mixture of step (d) until the ingredients are uniformly dispersed throughout the mixture; and (f) mixing sufficient water to the mixture of step (e) to produce an aqueous pharmaceutical suspension of 100% desired volume.

DETAILED DESCRIPTION OF THE INVENTION

The invention will now be described specifically in terms of its most preferred embodiments which is the preparation of aqueous suspensions of ibuprofen. Ibuprofen is a medicament used in both over-the-counter preparations and in prescription drugs for analgesic and antipyretic purposes. Ibuprofen is generally indicated for the temporary relief of minor aches and pains associated with the common cold, headache, toothaches, muscular aches, backache, for minor pain of arthritis, for the pain of menstrual cramps and for the reduction of fever. Reference will also be made in detail herein to other preferred embodiments of the compositions, processes and methods of the invention.

Aqueous suspension oral dosage forms for water insoluble or sparingly water soluble drugs are particularly advantageous since they can be alcohol free and provide an alternate means to tablets, caplets, and capsules for oral dosage. Ibuprofen is the most preferred water insoluble pharmaceutical active useful in accordance with the invention. Ibuprofen is substantially water insoluble at pH's below 6. For the purposes of the present invention the term substantially water insoluble refers to compositions which are insoluble, practically insoluble or only slightly soluble in water. This solubility can be at certain pH's e.g. 3.5 to 6 for ibuprofen, or cover a narrower or broader range of pH to determine water insolubility. Examples of other water insoluble pharmaceutical actives that can be used in accordance with the invention include but are not limited to the following examples: cardiovascular drugs, e.g. cardiac glycosides, clofibrate and probucol; hypoglycemic drugs; sedatives/hypnotics, e.g. barbiturates, disulfiram and glutethimide; antiepileptics, e.g., carbamazepine, mephenytoin, phenytoin and phensuximide; psycholpharmacologic agents e.g. perphenazine; analgesic, antipyretic and anti-inflammatory agents, e.g. naproxen, oxycodone, indomethacin, and phenylbutazone; antineoplastic drugs such as lomustine; and antimicrobials such as erythromycin estolate.

The aqueous pharmaceutical suspension composition in accordance with the present invention comprises from about 0.2% to about 20.0% of the substantially water insoluble pharmaceutical active. This amount is based in general terms on effective amounts of pharmaceutical actives such that suspensions containing less than 0.2% of pharmaceutical actives are possible. Amounts of pharmaceutical active in this range are generally acceptable for taste masking but it is possible that more than 20% of a water insoluble pharmaceutical active could be included in the suspension and be sufficiently taste masked for consumer acceptability.

Stabilizing the suspension of water insoluble pharmaceutical actives is the key inventive step of the present invention. It has been found by the present inventor, that the unique combination of xanthan gum, pregelatinized starch and a surfactant such as polyoxyethylene sorbitan monooleate produces advantageously storage stable and homogeneously dispersed suspensions of water insoluble pharmaceutical actives.

Xanthan gum is a high molecular weight natural carbohydrate, specifically, a polysaccharide. Xanthan gum is a known suspension stabilizer by itself for suspending fruit pulp in drinks and concentrates, calamine lotions, preventing settling in food toppings, salad dressings and syrups.

Pregelatinized starch is prepared from modified, stabilized and waxy, maize food starch. Pregelatinized starch is precooked so that it swells and begins to thicken instantly when added to cold water. The pregelatinized starch component used in combination with xanthan gum in accordance with the present invention has been found to provide superior storage stable and homogeneously dispersed suspensions of water insoluble pharmaceutical actives.

The preferred surfactant used in accordance with the invention is a sorbitan oleate ester, particularly, polyoxyethylene sorbitan monooleate also known as polysorbate 80. Such surfactants or surface active molecules consist of two ends or parts: a polar or ionic group at one end and a non-polar organic chain at the other end. Each part of the surfactant has an affinity for a different phase of the aqueous suspension. Once wetted by the aqueous phase, the surfactant provides stability by what is known as steric stabilization. The non-polar group adsorbs onto the non-wetting hydrophobic surface of the solid phase and the polar end extends into the aqueous phase. This dual absorption allows the suspended particles to be surrounded by water molecules and incorporated into the aqueous solution. In accordance with the present invention the suspension is stabilized by a mixture of suspension stabilizing effective amounts of xanthan gum, pregelatinized starch and polyoxyethylene sorbitan monooleate. Preferably the suspension stabilizing effective amount of these components comprises from about 1.25 to about 1.90% weight by volume of the total suspension. In particular, the xanthan gum would comprise about 0.13 to 0.24%, the preglatinized starch about 1.05 to 1.60%, and the polyoxyethylene sorbitan monooleate about 0.01 to 1.00% weight by volume of the total suspension. These amounts will vary as other amounts of components will vary according to the type and amount of pharmaceutical active desired to be incorporated into the suspension as well as the amount of taste masking and sweetness desired for the pharmaceutical suspension.

Taste masking components generally comprise from about 25 to 50% by weight by volume of the total composition. The present invention however is not limited to this amount but rather to an effective amount of the taste masking composition to produce a consumer acceptable suspension. For example, if highly intense artificial sweeteners are used a lesser amount would be required then would be the case for sugars to achieve effective taste masking. The amount of taste masking required would vary with the amount of pharmaceutical active used as well as the intensity of the poor taste of the pharmaceutical active. If a particular pharmaceutical active is substantially taste neutral then the amount of taste masking composition required could be greatly reduced. Preferred taste masking compositions in accordance with the invention include but are not limited to sugars, sweet polyhydric alcohols, (glycerin), artificial sweetener, flavoring agents and mixtures thereof. Examples of sugars include sucrose, fructose, dextrose, and glucose. Examples of sweet polyhydric alcohols include glycerin sorbitol and mannitol. The type of glycerin preferably used is U.S.P. grade. Examples of artificial sweetners include aspartame, sucralose, cyclamates, saccharin and mixtures thereof. Examples of flavoring agents include natural and artificial fruit flavors.

Citric acid is a preferred ingredient to add to the suspension to stabilize the pH of the suspension at between 3.5 and 5.0. Citric acid is advantageously added since a lower pH (i.e. 3.5 to 5.0) will prevent microbial growth and add to the stability of the product. A preferred pH for the suspension when ibuprofen is the substantially water insoluble pharmaceutical active used is between 3.5 and 5.0 since the ibuprofen will remain water insoluble and in suspension at this microbial inhibiting pH.

The present invention also provides a process for preparing the aqueous pharmaceutical suspension composition. The preferred process comprises the following sequential steps:

(a) dry blending from about 0.13 to 0.24% xanthan gum, about 0.05 to 1.60% pregelatinized starch and from about 4% to 7% sugar, preferably sucrose, by weight by volume of the total suspension;

(b) separately mixing about 50% water, 5 to 30% glycerin, and 0 to 10% of a sweet polyhydric alcohol, preferably sorbitol, by weight by volume of the total suspension;

(c) adding the dry blend of step (a) with the aqueous mixture of step(b) and mixing until the xanthan gum and pregelatinized starch are uniformly dispersed throughout the mixture;

(d) adding from about 16 to 28% sugar, preferably sucrose, by weight by volume of the total suspension to the dispersion of step (c) and mixing until the ingredients are uniformly dispersed in the mixture;

(e) admixing about 0.01 to 1.00% polyoxyethylene sorbitan monooleate, about 0.2 to about 20.0% preferably 0.4 to about 10.0% of a substantially water insoluble pharmaceutical active, preferably ibuprofen by weight by volume of the total suspension and sufficient citric acid to lower the pH of the solution to between about 3.5 to 5.0 to the mixture of step (d) until the ingredients are uniformly dispersed throughout the mixture; and (f) adding and mixing sufficient water to the mixture of step (e) to produce an aqueous pharmaceutical, preferably ibuprofen, suspension of 100% desired volume.

In preferred embodiments of the process an effective amount of preservative such as, for example, benzoic acid, and its salts including sodium benzoate, or sorbic acid and its salts, is added to the mixture in step (e) and the suspension in step (f) is subjected to a deaerating step so that the volume of the suspension is adjusted to 100% by addition of water after such deaerating. Preferably the flavoring and coloring ingredients added to the mixture in step (e) are of the type and amount desired for the particular suspension to meet the preferences dictated by the intended consumer of such suspension e.g. pediatric or adult. A more detailed example of the preferred process of the invention as carried out with ibuprofen and tolmetin as the active ingredients is provided in the following examples section.

EXAMPLES

The invention will now be illustrated by examples. The examples are not intended to be limiting of the scope of the present invention but read in conjunction with the detailed and general description above, provide further understanding of the present invention and an outline of a preferred process for preparing the compositions of the invention. Example 1—Ibuprofen Suspension Liquid Dosage Form

| Ingredients | Unit Amount (gm. %) | Batch Amount (grams) |
|---|---|---|
| Ibuprofen, USP | 2.0 | 7570.0 |
| Glycerin, USP | 10.0 | 37850.0 |
| Sucrose, Granular, NF, (Beet) | 30.0 | 113550.0 |
| Pregelatinized Starch (CLEARJEL) | 1.31 | 4958.40 |
| Xanthan Gum, NF, (KELTROL-T) | 0.18 | 681.30 |
| Polysorbate 80, NF, (TWEEN 80) | 0.05 | 189.25 |
| Citric Acid, anhydrous, USP | 0.18 | 681.30 |
| Sodium Benzoate, NF | 0.20 | 757.0 |
| Artificial Flavorings | 0.43 | 1627.55 |
| FD&C Yellow #10 | 0.0025 | 9.463 |
| FD&C Red #40 | 0.0009 | 3.407 |
| Purified Water, USP | qs to: 100.00 ml. | 378.5 Liters |

Processing Directions

1. Dry blend in a suitable blender, 20% granular sucrose (22.53 kg.) with the pregelatinized starch and xanthan gum, for 10 minutes.

2. To a tared pot, add 200.0 liters of purified water and glycerin, and mix approximately 2-3 minutes.

3. Add the dry blend mixture, (gums and sucrose), and mix until gums are dispersed, approximately 10-15 minutes.

4. Add the remaining sucrose, (90.72 kg.), and mix until dissolved, approximately 10-15 minutes. Take in-process viscosity 1966.4 cps.

5. Add polysorbate 80, citric acid and sodium benzoate and mix approximately 5-10 minutes.

6. Add ibuprofen (screened through 40 mesh), and mix approximately 15 minutes.

7. Add flavors and mix approximately 5 minutes.

8. Add dyes, FD&C red #40, and FD&C Yellow #10, (premixed in purified water,), and mix approximately 5 minutes.

9. Bring suspension to near final volume with 56.7 liters purified water, and mix approximately 10 minutes.

10. Let suspension deaerate overnight, approximately 12-16 hours.

11. Bring suspension to final volume with 10.6 liters purified water, and mix approximately 10 minutes.

The above produces a batch size of approximately 378.5 liters or 100 gallons of ibuprofen suspension (100 mg/5 ml ) at a pH of 3.97.

Example 2—Preparation Of Ibuprofen Suspension Liquid Drop Dosage Form

| Ingredients | Unit Amount (gm. %) | Batch Amount (grams) |
|---|---|---|
| Ibuprofen, USP | 4.0 | 15140.0 |
| Glycerin, USP | 5.0 | 18925.0 |
| Sorbitol Solution | 5.0 | 18925.0 |
| Sucrose, Granular, NF (Beet) | 30.0 | 113550.0 |
| Pregelatinized Starch (CLEARJEL) | 1.2 | 4542.0 |
| Xanthan Gum, NF, (Keltrol-T) | 0.2 | 757.0 |
| Polysorbate NF (TWEEN 80) | 0.05 | 189.25 |
| Citric Acid, anhydrous, | 0.18 | 681.30 |

| Ingredients | Unit Amount (gm. %) | Batch Amount (grams) |
|---|---|---|
| USP | | |
| Sodium Benzoate, NF | 0.20 | 757.0 |
| Artificial Flavorings | 0.86 | 3255.1 |
| FD&C Red #40 | 0.001 | 3.785 |
| Purified Water, USP Liters | qs to: 100.0 | 378.5 |

PROCESSING DIRECTIONS

1. Dry blend in a suitable blender, 20% granular sucrose, (22.83 kg.) with the pregelatinized starch and the xanthan gum for 10 minutes.
2. To a tared pot, add 193.5 liters of purified water glycerin and sorbitol solution, and mix approximately 2–3 minutes.
3. Add the dry blend mixture (gums and sucrose), and mix until gums are dispersed, approximately 10–15 minutes.
4. Add the remaining sucrose, (90.72 kg.), and mix until dissolved, approximately 10–15 minutes. Take in-process viscosity 1513.2 cps.
5. Add polysorbate 80, citric acid, sodium benzoate, and mix approximately 5–10 minutes.
6. Add ibuprofen (screened through 40 mesh) and mix approximately 15 minutes.
7. Add flavors and mix approximately 5 minutes.
8. Add FD&C Red #40 dye, premixed in purified water and mix approximately 5 minutes.
9. Bring suspension to near final volume with 47.6 liters purified water and mix approximately 10 minutes.
10. Let suspension deaerate overnight, approximately 12–16 hours.
11. Bring suspension to final volume with 12.2 liters purified water USP, and mix approximately 10 minutes.

The above produces a batch size of 378.5 Liters ibuprofen suspension drops (40 mg/ml) at a pH of 3.92.

Example 3—Tolmetin Liquid Suspension Dosage Form

The process of Example 1 is carried out except that 7.570 kg. of tolmetin is substituted for ibuprofen to produce 100 mg/5 ml tolmetin suspension.

The scope of the present invention is not limited by the description, examples and suggested uses herein and modifications can be made without departing from the spirit of the invention. For example, additional medicaments may be added to the aqueous suspension to provide a combination medication. Further, the pharmaceutical suspension of the invention may be utilized for non-medicament ingredients including nutrients such as vitamins and minerals.

Application of the compositions and method of the present invention for medical and pharmaceutical uses can be accomplished by any clinical, medical and pharmaceutical methods and techniques as are presently or prospectively known to those skilled in the art. Thus it is intended that the present invention cover the modifications and variations of this invention provided that they come within the scope of the appended claims and their equivalents.

What is claimed is:

1. An aqueous pharmaceutical suspension composition consisting essentially of: from about 0.2 to 20.0% weight by volume of the total suspension of a substantially water insoluble pharmaceutical active selected from the group consisting of analgesics, antipyretics, and anti-inflammatory agents; from about 0.13 to 0.24% weight by volume of the total suspension xanthan gum; from about 1.05 to 1.60% weight by volume of the total suspension pregelatinized starch; from about 0.01 to 1.00% weight by volume of the total suspension polyoxyethylene sorbitan monooleate; an effective amount of a taste masking composition selected from the group consisting of sugar, sweet polyhydric alcohol, cyclamates, aspartame, sucralose, saccharin, flavoring agents and mixtures thereof; and water.

2. A composition according to claim 1 wherein the taste masking composition comprises from about 25 to 50% by weight by volume of the total suspension.

3. A composition according to claim 1 wherein the taste masking composition comprises from about 20 to 35% sucrose, from about 0 to about 10% sorbitol and from about 5 to about 30% glycerin weight by volume of the total suspension.

4. A composition according to claim 1 wherein the suspension additionally comprises citric acid in an amount effective to stabilize the pH of the suspension at between 3.5 and 5.0.

5. An aqueous ibuprofen suspension composition consisting essentially of: from about 0.4% to about 20.0% ibuprofen, from about 0.13 to 0.24% xanthan gum, from about 1.05 to 1.60% pregelatinized starch and from about 0.01 to 1.0% polyoxyethylene sorbitan monooleate weight by volume of the total suspension; and an effective amount of a taste masking composition selected from the group consisting of sugar, sweet polyhydric alcohol, cyclamates, aspartame, sucralose, saccharin, flavoring agents and mixtures thereof, citric acid in an amount effective to maintain the pH of the suspension in the range of from about 3.5 to 5.0; and water.

6. A composition according to claim 5 wherein the taste masking composition comprises from about 25 to 50% by weight by volume of the total suspension.

7. A composition according to claim 5 wherein the taste masking composition comprises from about 20 to 35% sucrose, from about 0 to 10% sorbitol and from about 5 to 30% glycerin, by weight by volume of the total suspension.

8. An aqueous ibuprofen suspension composition consisting essentially of: from about 0.4% to 10.0% ibuprofen, about 0.13 to 0.24% xanthan gum, about 1.05 to 1.60% pregelatinized starch and about 0.01 to 1.00% polyoxyethylene sorbitan monooleate weight by volume of the total suspension; about 20 to 35% sucrose and about 0 to 10% sorbitol weight by volume of the total suspension; and about 5 to 30% glycerin weight by volume of the total suspension; citric acid in an amount effective to maintain the pH of the suspension in the range of from about 3.5 to 5.0; and water.

9. The suspension of claim 8 comprising about ibuprofen, 0.18% xanthan gum, 1.31% pregelatinized starch and 0.05% polyoxyethylene sorbitan monooleate weight by volume of the total suspension.

10. The composition of claim 1 wherein the pharmaceutical active is selected from the group consisting of: ibuprofen, tolmetin, naproxen, oxycodone, indomethacin, and phenylbutazone.

11. The composition of claim 1 wherein pharmaceutical active is an analgesic.

12. The composition of claim 1 wherein the pharmaceutical active is an antipyretic.

13. The composition of claim 1 wherein the pharmaceutical active is an anti-inflammatory agent.

* * * * *

UNITED STATES PATENT AND TRADEMARK OFFICE
CERTIFICATE OF CORRECTION

PATENT NO. : 5,374,659
DATED : December 20, 1994
INVENTOR(S) : Walter G. Gowan, Jr.

It is certified that error appears in the above-indentified patent and that said Letters Patent is hereby corrected as shown below:

Column 8, line 54, after "about" insert -- 2.0% --

Signed and Sealed this

Nineteenth Day of September, 1995

Attest:

BRUCE LEHMAN

Attesting Officer

Commissioner of Patents and Trademarks